(12) United States Patent
Son

(10) Patent No.: US 9,770,149 B2
(45) Date of Patent: Sep. 26, 2017

(54) ROBOT CLEANER AND METHOD FOR SENSING DUST

(71) Applicant: LG ELECTRONICS INC., Seoul (KR)

(72) Inventor: Kuyoung Son, Seoul (KR)

(73) Assignee: LG ELECTRONICS INC., Seoul (KR)

( * ) Notice: Subject to any disclaimer, the term of this patent is extended or adjusted under 35 U.S.C. 154(b) by 226 days.

(21) Appl. No.: 14/515,772

(22) Filed: Oct. 16, 2014

(65) Prior Publication Data

US 2015/0107449 A1    Apr. 23, 2015

(30) Foreign Application Priority Data

Oct. 21, 2013 (KR) .......................... 10-2013-0125487

(51) Int. Cl.
*A47L 9/00* (2006.01)
*G01N 27/22* (2006.01)
(Continued)

(52) U.S. Cl.
CPC .............. *A47L 9/0072* (2013.01); *A47L 9/10* (2013.01); *A47L 9/122* (2013.01); *A47L 9/19* (2013.01);
(Continued)

(58) Field of Classification Search
CPC combination set(s) only.
See application file for complete search history.

(56) References Cited

U.S. PATENT DOCUMENTS 5,247,827 A * 9/1993 Shah .................. G01N 15/0656
                                                    73/28.01
5,935,179 A * 8/1999 Kleiner .................. G01S 7/521
                                                    340/943
(Continued)

FOREIGN PATENT DOCUMENTS

CN        1986070        6/2007
CN        201042409 Y    4/2008
(Continued)

OTHER PUBLICATIONS

Korean Notice of Allowance issued in application No. 10-2013-0125487 dated Dec. 10, 2014.
(Continued)

*Primary Examiner* — Duane Smith
*Assistant Examiner* — Sonji Turner
(74) *Attorney, Agent, or Firm* — KED & Associates LLP

(57) ABSTRACT

A robot cleaner is provided that may include a suction motor installed within a main body to generate a suction force, at least two conductive plates spaced apart from each other to form a flow path for external air introduced by the suction force, and a calculator to measure a capacitance value between the at least two conductive plates. Further, provided is a robot cleaner that may include a suction motor installed within a main body to generate a suction force, a porous structure having at least one through hole, through which external air introduced by the suction force may flow, at least one filter disposed on a surface of the porous structure to filter dust contained in the air, and a power supply configured to apply alternating current (AC) power to at least a portion of the surface of the porous structure.

7 Claims, 7 Drawing Sheets

(51) Int. Cl.
*B03C 3/66* (2006.01)
*A47L 9/12* (2006.01)
*A47L 9/19* (2006.01)
*A47L 9/20* (2006.01)
*A47L 9/28* (2006.01)
*A47L 9/10* (2006.01)
*B03C 3/017* (2006.01)
*H03K 17/955* (2006.01)

(52) U.S. Cl.
CPC .............. *A47L 9/20* (2013.01); *A47L 9/281* (2013.01); *A47L 9/2805* (2013.01); *A47L 9/2836* (2013.01); *A47L 9/2857* (2013.01); *B03C 3/017* (2013.01); *B03C 3/66* (2013.01); *G01N 27/22* (2013.01); *H03K 17/955* (2013.01); *A47L 2201/00* (2013.01)

(56) References Cited

U.S. PATENT DOCUMENTS

| | | | | |
|---|---|---|---|---|
| 6,956,348 | B2* | 10/2005 | Landry | A47L 9/2805 15/319 |
| 7,288,912 | B2* | 10/2007 | Landry | A47L 9/2805 15/319 |
| 7,459,871 | B2* | 12/2008 | Landry | A47L 9/2805 15/319 |
| 8,253,368 | B2* | 8/2012 | Landry | A47L 9/2805 15/319 |
| 8,378,613 | B2* | 2/2013 | Landry | A47L 9/2805 15/327.5 |
| 8,456,125 | B2* | 6/2013 | Landry | A47L 9/2805 15/319 |
| 9,144,361 | B2* | 9/2015 | Landry | A47L 9/2805 |

FOREIGN PATENT DOCUMENTS

| | | | |
|---|---|---|---|
| CN | 201101947 | Y | 8/2008 |
| CN | 101585015 | | 11/2009 |
| CN | 103282095 | | 9/2013 |
| DE | 10 2011 050 358 | A1 | 11/2012 |
| JP | H1-153131 | * | 6/1989 |
| JP | H 1-153131 | A | 6/1989 |
| JP | 2004-173962 | A | 6/2004 |
| JP | 2007-75581 | A | 3/2007 |
| JP | 2008-296221 | A | 12/2008 |
| JP | 2012-147854 | A | 8/2012 |
| KR | 20020025339 | A * | 4/2002 |
| KR | 20-0377890 | Y1 | 3/2005 |
| KR | 10-2011-0053765 | A | 5/2011 |
| KR | 10-2012-0027543 | A | 3/2012 |
| SU | 1589141 | * | 8/1990 |
| WO | WO 2007/074035 | A1 | 7/2007 |

OTHER PUBLICATIONS

European Search Report issued in application No. 14188747.1 dated Feb. 20, 2015.
Chinese Office Action dated Aug. 3, 2016 issued in Application No. 201410543392.6 (with English translation).

* cited by examiner

ROBOT CLEANER AND METHOD FOR SENSING DUST

CROSS-REFERENCE TO RELATED APPLICATION(S)

Pursuant to 35 U.S.C. §119(a), this application claims priority to Korean Application No. 10-2013-0125487, filed in Korea on Oct. 21, 2013, the contents of which is incorporated by reference herein in its entirety.

BACKGROUND

1. Field

A robot cleaner and a method for sensing dust are disclosed herein.

2. Background

Robot cleaners are known. However, they suffer from various disadvantages.

BRIEF DESCRIPTION OF THE DRAWINGS

Embodiments will be described in detail with reference to the following drawings in which like reference numerals refer to like elements, and wherein.

DETAILED DESCRIPTION

Figure 1:
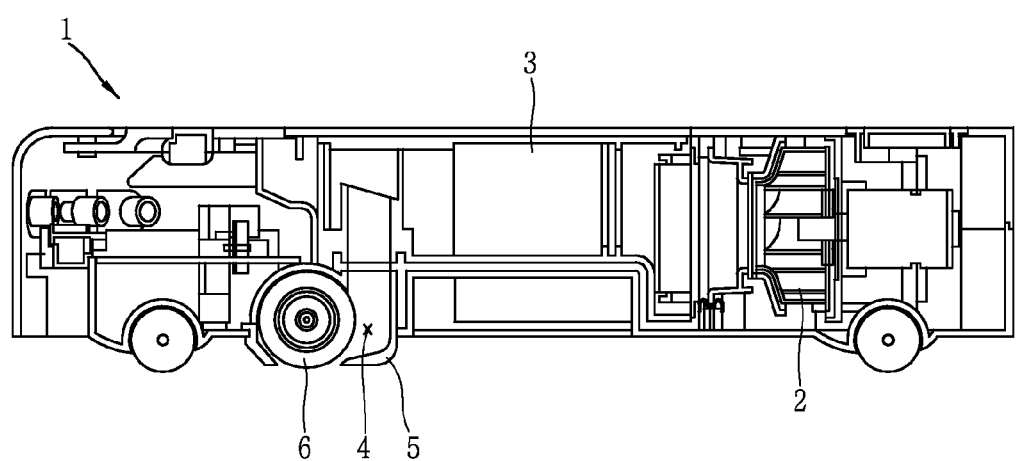
FIG. 1 is a longitudinal view of a robot cleaner.

Hereinafter, embodiments will be described in detail with reference to the accompanying drawings. The same or similar elements are designated with the same or similar reference numerals, and repetitive description has been omitted. Hereinafter, the terms "module" and "unit or portion" used for components herein are merely provided to facilitate the preparation of this specification, and thus, they are not granted a specific meaning or function. Hence, it should be understood that "module" and "unit or portion" may be used together. In describing embodiments, detailed description has been omitted for publicly known technologies. Also, it should be noted that the accompanying drawings are merely illustrated to easily explain the embodiments, and therefore, they should not be construed to limit the embodiments.

In general, robots have been developed for industrial use and have been responsible in part for factory automation. In recent times, with further extension of robot-applied fields, medical robots and space aerial robots have been developed, and household robots which can be used at ordinary homes are also under production.

A representative example of a household robot is a robot cleaner. A robot cleaner is a type of electronic device which carries out cleaning by sucking up dust or foreign materials around it while traveling (moving) around a predetermined area by itself.

FIG. 1 is a longitudinal view of a robot cleaner. Referring to FIG. 1, the robot cleaner 1 may include a suction motor 2 installed therein to generate a suction force, a dust container 3 installed at a front of the suction motor 2 to collect therein dust or dirt sucked in by the suction motor 2, a suction head 5 located at a lower side of the robot cleaner 1 and connected to the dust container 3 by a connection pipe 4 to suck dust or foreign materials on a floor therethrough, a pair of wheels 6 provided to move a main body, and at least one auxiliary wheel (not illustrated) configured to support the robot cleaner 1 and simultaneously horizontally balance the robot cleaner 1. The robot cleaner 1 may further include a driving unit or drive (not illustrated) configured to provide a drive force to the wheels, such that the main body of the robot cleaner 1 may be rotated or moved.

Figure 2:
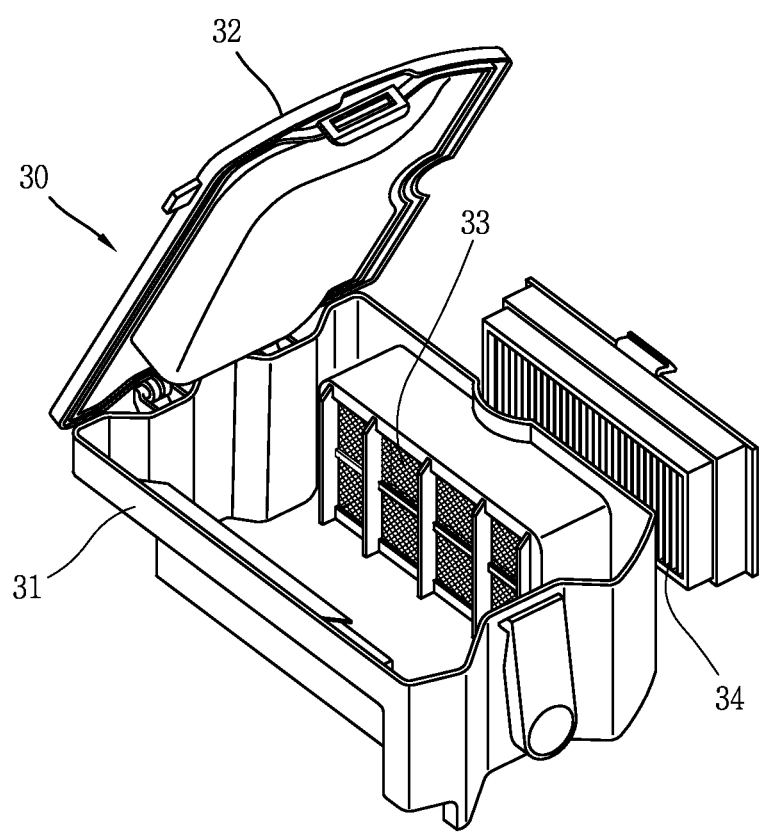
FIG. 2 is a perspective view illustrating a dust container used in a robot cleaner.

FIG. 2 is a perspective view of dust container used in a robot cleaner. As illustrated in FIG. 2, a dust container 30 may include a main body casing 31, and a cover 32 provided at one side of the casing 31 to open and close the casing 31. The dust container 30 may further include a check valve (not illustrated) disposed at one side within the casing 31 to form an inlet through which external air containing dust may be introduced, and filters 33 and 34 disposed at an inside or an outside of the casing 31 to filter dust before the sucked external air is discharged. The dust or dirt sucked in may be collected in the dust container 30 by virtue of the filters 33 and 34, and the air sucked in along with the dust may be discharged out of the robot cleaner 1 through the filters 33 and 34.

Based on the flow of the air which has been sucked in from the outside along with dust, the filters 33 and 34 may include a first filter 33 located at a front side, which may have a mesh form, and a second filter 34 located at a rear side, which may have a wrinkled form. The first filter 33 may filter large dust particles contained in the externally-sucked air. The air having passed through the first filter 33 may flow through the second filter 3, such that relatively small dust particles may be filtered, thereby being discharged out of the robot cleaner 1.

As the robot cleaner 1 repetitively carries out a cleaning process with respect to a cleaning area, the filters 33 and 34 may become covered with dust, which may lower a suction performance of the suction motor 2. That is, the suction motor 2 may maintain a predetermined suction force. However, the filters covered with dust may interfere with a flow path of the externally-sucked air. Consequently, to maintain the predetermined suction force, the drive force of the suction motor 1 has to be increased. This results in an increase in energy consumption by the suction motor 2. Therefore, technology to overcome such problems is desperately needed.

Figure 3:
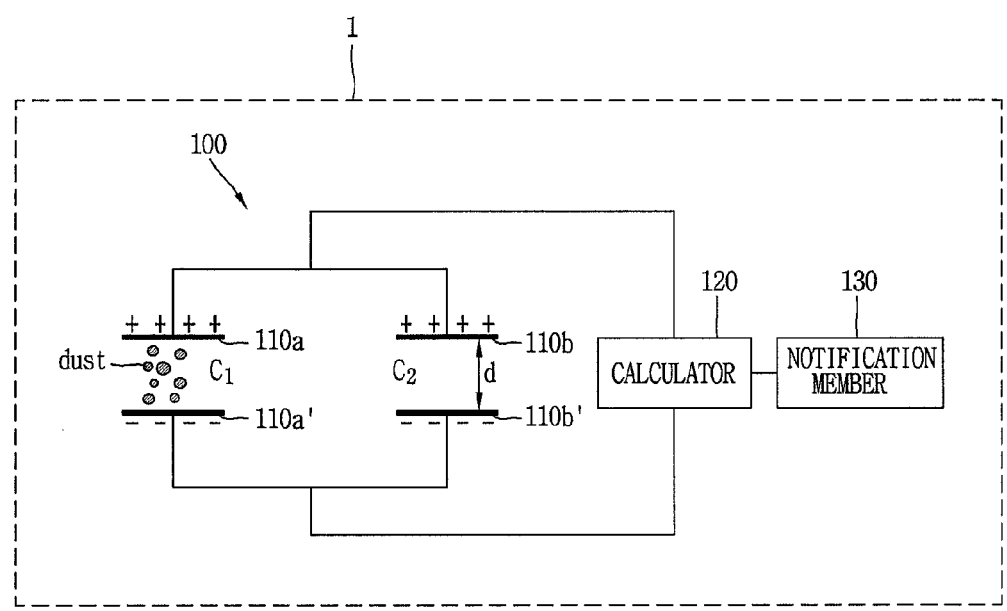
FIG. 3 is a schematic view of a dust sensing apparatus for a robot cleaner in accordance with an embodiment.

FIG. 3 is a schematic view of a dust sensing apparatus for a robot cleaner in accordance with an embodiment. As illustrated in FIG. 3, a dust sensing apparatus 100 for or equipped or provided in a robot cleaner according to an embodiment may include at least two conductive plates 110*a* and 110*a'*, 110*b* and 110*b'* spaced apart from each other, and a calculator 120 to calculate (measure) a capacitance (value) between the plates 110*a* and 110*a'*, 110*b* and 110*b'*. FIG. 3 shows two pairs of conductive plates 110*a* and 110*a'*, 110*b* and 110*b'*; however, embodiments are not limited thereto.

A space, which may be formed as the at least two conductive plates 110a and 110a', 110b and 110b' are spaced apart from each other, may form a flow path for air sucked in by the robot cleaner 1. Dust particles contained in the air passing through the flow path may be collected (piled, stacked, accumulated) on the plates 110a and 110a', 110b and 1101D'.

A capacitance value between the two plates 110a and 110a', 110b and 110b' may change according to an amount of dust collected on the plates 110a and 110a', 110b and 110b'. The changed capacitance value between the plates may be measured by the calculator 120, which may result in calculating an amount of dust collected on the at least two conductive plates and also indirectly calculating an amount of dust collected on a filter or in a dust container located near the conductive plates.

In detail, for example, a capacitance value between the two plates 110a and 110a', and 110b and 110b', which may be measured by the calculator 120, for example, may be expressed by the following Equation 1, assuming that the two plates are substantially parallel plates having a same shape.

$$C = C_1 + C_2 = \varepsilon_r \varepsilon_0 \frac{A}{d} \qquad \text{[Equation 1]}$$

where C denotes a capacitance value between the two plates 110a and 110a', and 110b and 110b', C1 denotes a capacitance value of one plate 110a and 110a', C2 denotes a capacitance value of one plate 110b and 110b, $\varepsilon_0$ denotes vacuum permittivity (or vacuum dielectric constant) ($\approx 8.854 \times 10^{-12}$ F/m), $\varepsilon_r$ denotes permittivity or a relative dielectric constant of a material between the two plates, A denotes an area of one plate, and d denotes a distance between the two plates.

The capacitance value with respect to the at least two conductive plates is proportional to the permittivity $\varepsilon$. The permittivity and the capacitance value depend on an amount of dust between the at least two plates. Therefore, an amount of dust collected (piled) between the plates and/or around the plates may be determined by the dielectric constant or the capacitance value calculated by the calculator 120. This is because the capacitance value increases in response to an increased thickness of dust which is stacked between the at least two conductive plates.

Also, when there is a considerable amount of dust in the dust container 30 in which dust is collected, dust may also be stacked (accumulated) between the two plates or on the filters located near the plates, which results in the increase in the capacitance value measured by the calculator 120. Therefore, based on the capacitance value, an amount of dust collected in the dust container 30 or an amount of dust stuck on the filters near the conductive plates may be estimated. In other words, an increase in an amount of dust collected in the dust container 30 brings about an increase in an amount of dust which is added while the externally-sucked air passes through the dust container 30. This results in more dust laying on the conductive plates.

To store electric charges, the at least two conductive plates 110a and 110a', 110b and 110b' may be formed in a shape such that the two plates may be disposed to extend substantially in parallel to each other, or in a shape such that two cylinders with different radiuses from each other may be coaxially arranged, for example. However, any shape may be suitable if the robot cleaner has a path for externally-sucked air.

Figure 4:
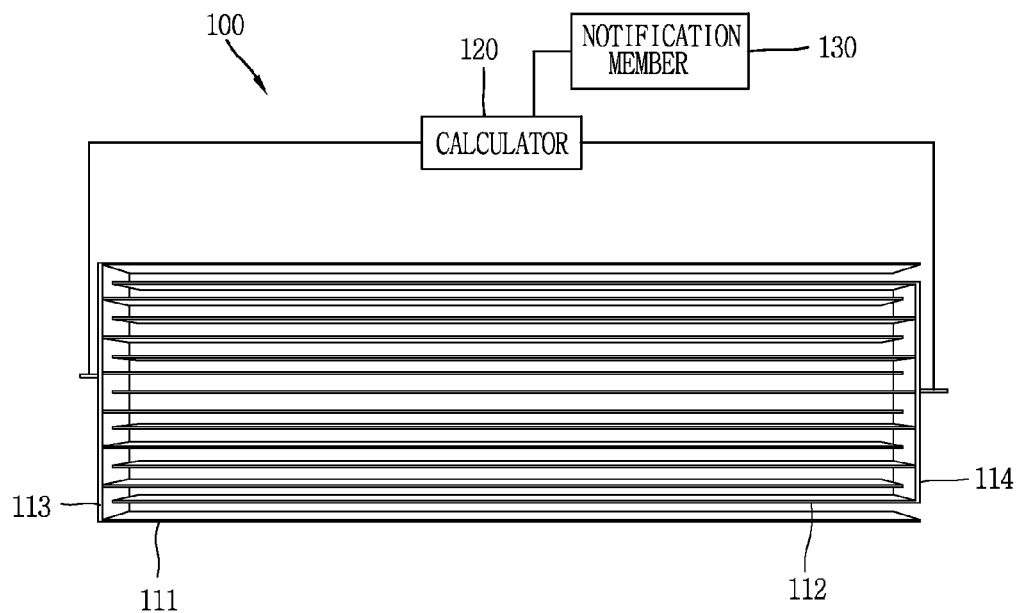
FIG. 4 is a view illustrating the dust sensing apparatus included in the robot cleaner in accordance with an exemplary embodiment.

For example, the at least two plates, as illustrated in FIG. 4, may have a shape of a plurality of parallel plate capacitors connected substantially in parallel. That is, a plurality of first plates 111 and second plates 112 may be alternately arranged substantially in parallel and spaced apart from each other. A first connector 113 may connect the plurality of first plates 111 as one or a first electrode (for example, (+) pole), and a second connector 114 may connect the plurality of second plates 112 as another or a second electrode (for example, (−) pole).

The plurality of first plates 111 and the plurality of second plates 112 may be arranged to be alongside of or to extend along a flow direction of air containing dust, introduced from one side thereof, or may be horizontally disposed with respect to the ground. This may allow dust contained in externally-introduced air to be smoothly laid on the conductive plates, without a reduction in a suction force, which is generated by the suction motor.

The dust sensing apparatus 100 included in the robot cleaner according to embodiments disclosed herein may further include a dust remover, which will be described hereinbelow. Accordingly, if the calculator 120 determines that a measured capacitance value has exceeded a predetermined value, the dust remover may apply Alternating Current (AC) power to at least a portion of a surface of a porous structure 210, so as to separate dust laid on the porous structure 210 and/or first to third filters 310 to 330 from them.

When the calculator 120 carries out a determination as to whether the capacitance value exceeds a predetermined value k, it may repeat the calculation (measurement) of the capacitance value a plurality of times at a predetermined time interval. The calculator 120 may determine whether a number of calculations reaches a predetermined number of times, for example, three times, so as to decide supply or non-supply of power to the porous structure 210 using a power supply 220. This may result in a more accurate determination as to whether dust collected between the at least two plates has exceeded a predetermined amount, thereby preventing an erroneous determination.

The dust sensing apparatus 100 included in the robot cleaner according to embodiments disclosed herein may further include a notification member 130. The notification member 130 may be included in the calculator 120 or electrically connected to the calculator 120. When the capacitance value between the at least two conductive plates, calculated by the calculator 120, exceeds the predetermined value, the notification member 130 may generate sound or light to the outside, such that a user may audibly or visibly recognize requirements for cleaning the dust container, the conductive plates, the porous structure, and/or the at least one filter.

Figure 5:
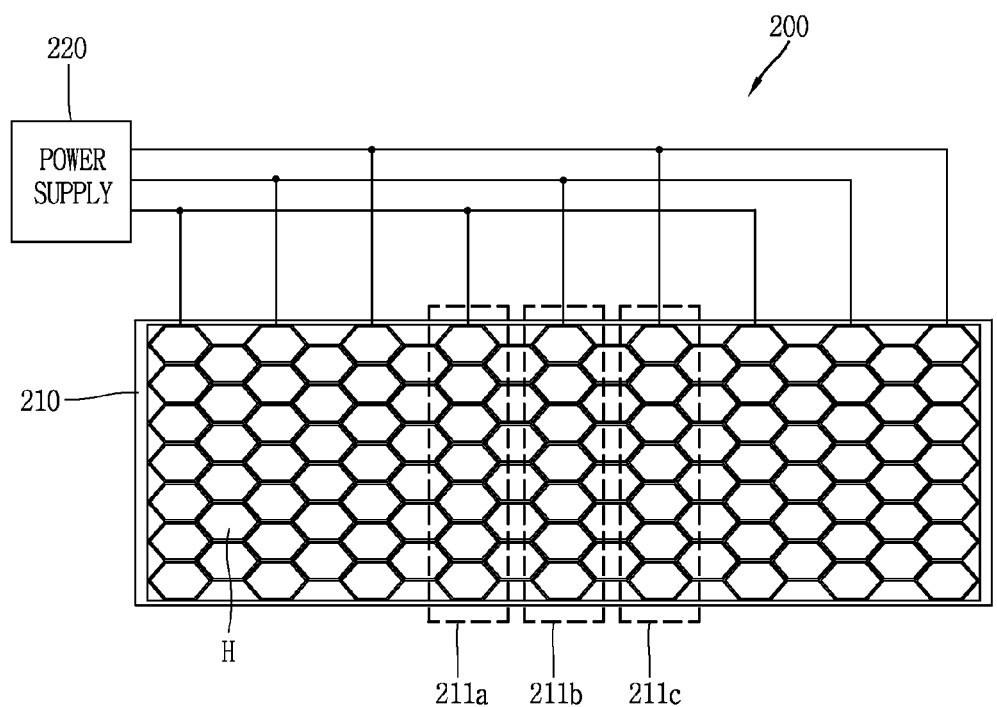
FIG. 5 is a schematic view of a dust remover included in a robot cleaner in accordance with an embodiment.

FIG. 5 is a schematic view of a dust remover included in a robot cleaner in accordance with an embodiment. As illustrated in FIG. 5, a dust remover included in a robot cleaner according to embodiments disclosed herein may include a porous structure 210 and a power supply unit 220.

The porous structure 210 may include at least one through hole H, through which external air sucked in by the robot cleaner may flow. The power supply 220 may apply AC power to at least a portion of a surface of the porous structure 210 (including at least a portion of an inner circumferential surface and/or outer circumferential surface of the through hole H). In response to the AC power being applied from the power supply 220 to the at least a portion of the surface of the porous structure 210, an electric field may be generated. Due to the generation of the electric field, dust laid on the porous structure 210, the conductive plates, and/or adjacent filters may be separated therefrom.

Figure 6A:
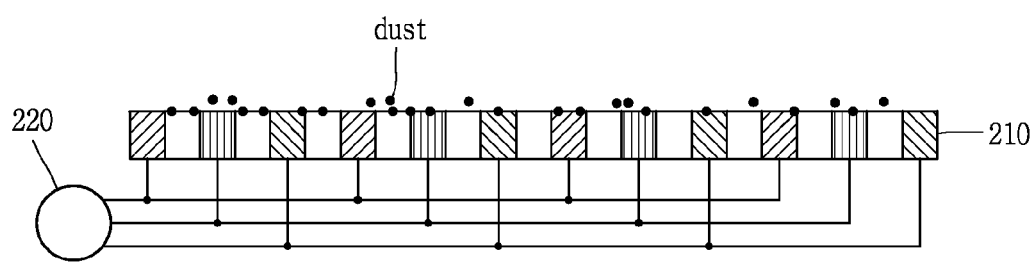
FIGS. 6A and 6B are diagrams illustrating a process of removing dust from a porous structure in accordance with an embodiment.
Figure 6B:
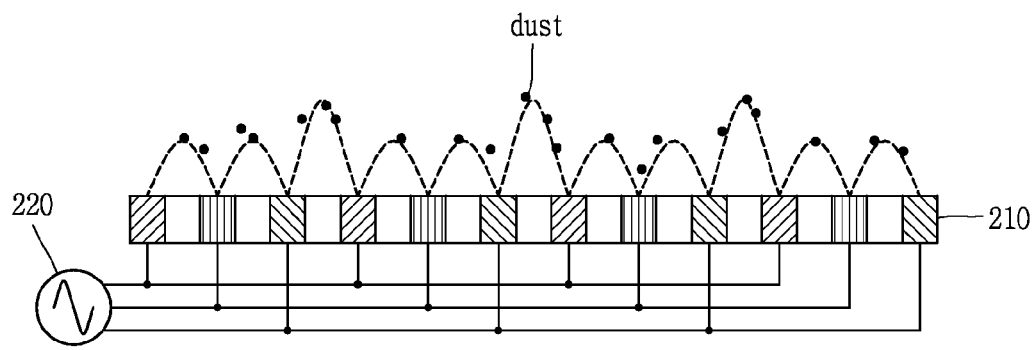

Among the dust laid on the porous structure 210, the conductive plates, and/or the adjacent filters, electrically-charged dust particles may be separated from a portion on which the dust particles are laid, collected, or accumulated, due to an electric force caused by the AC power with positive and negative poles. Electrically-non-charged dust particles may be electrically charged due to being repetitively collided with various insulators by various forces applied from the exterior, and then, may be separated from the portion due to an electric force generated by the AC power later applied. Various types of dust particles, as illustrated in FIG. 6A, which may be stuck on the porous structure 210 or filters (not illustrated) adjacent to the porous structure 210 due to static electricity, may be separated from the porous structure 210, the conductive plates, and/or the adjacent filters, by applying the AC power from the power supply 220 to at least a portion of the surface of the porous structure 210, as illustrated in FIG. 6B.

The porous structure 210 may be formed, for example, in a mesh shape with a plurality of through holes arranged into a form of a net, but as illustrated in FIG. 5, may have a honeycomb structure. The porous structure 210 having the honeycomb structure may provide advantages in that external air sucked by the robot cleaner may flow smoothly therethrough and rigidity against an external force may be ensured or provided.

The porous structure 210, as illustrated in FIG. 5, may include at least one conducting portion 211a, 211b, 211c, which may be formed on at least a portion of the surface of the porous structure 210, such that the AC power applied from the power supply 220 may be received.

The at least one conducting portion 211a, 211b, 211c may be formed in a predetermined shape on the at least a portion of the surface of the porous structure 210. For example, the at least one conducting portion 211a, 211b, 211c may be formed along an outer circumferential surface and/or an inner circumferential surface of the plurality of through holes H.

When the power supply 220 supplies n-phase AC power, such AC power is applied to n-numbered conducting portions for each phase. Power with a phase difference by a predetermined phase angle may be supplied to each of the conducting portions 211a, 211b and 211c sequentially from one side of the porous structure 210. In detail, when the power supply 220 supplies three-phase power, the first to third conducting portions 211a to 211c may be sequentially supplied with single-phase power having a phase difference of 0°, power having a phase difference of ±120°, and power having a phase difference of ±240°, based on the single-phase power of 0° according to each position thereof. That is, the single-phase power having phase angles 0°, 120°, and 240° may be applied to the first to third conducting portions 211a to 211c, respectively.

By applying the single-phase power, which has a predetermined phase difference based on a predetermined single-phase power, to the conducting portions 211a to 211c sequentially according to their positions, when dust particles are separated from the porous structure 210 and the adjacent filters due to an electromagnetic force, the dust particles may be separated along a direction dependent on a wavelength direction, which may result in an improvement of separation (escape, removal) efficiency of the dust particles.

As aforementioned, the dust remover included in the robot cleaner according to embodiments disclosed herein may include a filter (not illustrated) to filter dust contained in external air sucked in by the robot cleaner. The filter may be located on one surface of the porous structure 210, or spaced apart from the one surface of the porous structure 210 by a predetermined gap.

A plurality of filters may be provided. The plurality of filters may have mesh holes of different sizes, be formed of different materials, or have different shapes, to filter dust particles of different sizes.

Such filters will be discussed hereinbelow.

Similarly, the dust remover included in the robot cleaner according to embodiments disclosed herein may further include a dust sensing apparatus. When the calculator 120 determines that a measured capacitance value has exceeded a predetermined value, the power supply 220 may apply AC power to the at least a portion of the surface of the porous structure 210, thereby removing dust from the porous structure 210 and/or first to third filters 310 to 330.

Figure 7:
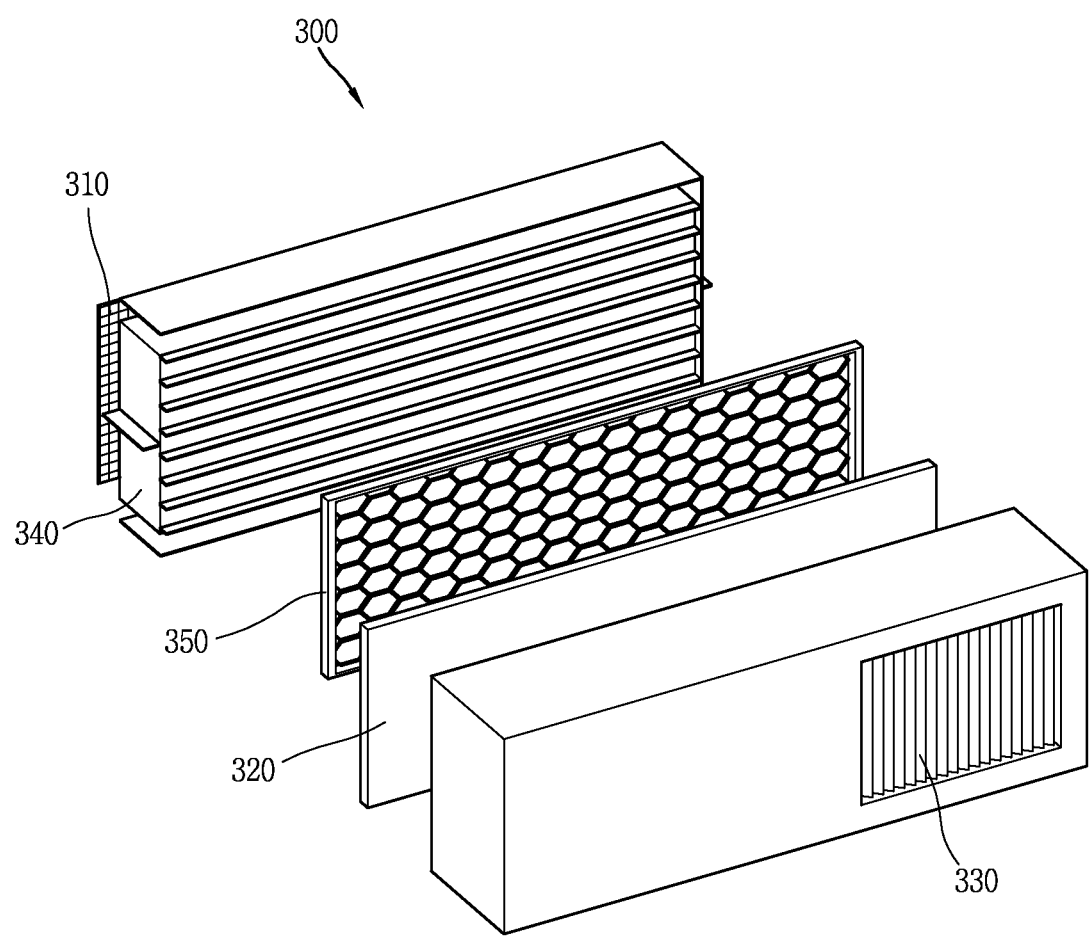
FIG. 7 is a perspective view of a filter assembly in accordance with an embodiment.

FIG. 7 is a perspective view of a filter assembly in accordance with an embodiment. As illustrated in FIG. 7, a filter assembly 300 according to embodiments may include a plurality of conductive plates 340. The filter assembly 300 according to one embodiment may include a porous structure 350 provided with a through hole located at one side of the plurality of conductive plates 340 and formed along a flow direction of external air sucked in. The filter assembly 300 according to another embodiment may include both the plurality of conductive plates 340 and the porous structure 350.

The plurality of conductive plates 340 may be spaced apart from one another to form a flow path, through which external air sucked in by the robot cleaner may flow. When dust contained in the external air sucked in is piled in a space formed by the plurality of conductive plates 340, which are spaced apart from one another, a capacitance value of the conductive plates 340 may differ according to the amount of dust piled up. The detailed structure of the plurality of conductive plates 340 may be the same as that disclosed with respect to the previous embodiment, and thus, detailed description thereof has been omitted.

The porous structure 350 may include at least one through hole through which external air sucked in by the robot cleaner may flow. AC power may be applied to at least a portion of the surface of the porous structure 350, such that dust stuck on the porous structure 350 and/or adjacent filters may be removed therefrom by a generated electric force.

Similarly, the detailed structure of the porous structure 350 may be the same as that disclosed with respect to the previous embodiment, and thus, detailed description thereof has been omitted.

The filter assembly 300 according to embodiments disclosed herein may further include a plurality of filters 310, 320, and 330, which may filter dust particles of different sizes contained in the external air sucked in by the robot cleaner 1.

In accordance with one embodiment, the first filter 310 of the plurality of filters 310, 320, and 330 may be a filter in a mesh form. The first filter 310 in the mesh form, in comparison with the second and third filters 320 and 330, may be formed with more than 70 mesh holes (the number of mesh holes belonging to a 1 cm×1 cm area), such that relatively large dust particles are not discharged out of the dust container.

Also, the second filter 320 of the plurality of filters 310, 320 and 330 may be configured to filter relatively small dust particles, in comparison to the first filter 310. The mesh holes of the second filter 320 may be smaller than the mesh holes of the first filter 310. For example, the second filter 320 may be cotton or a sponge in a pad shape.

The third filter 330 of the plurality of filters 310, 320, and 330 may be configured to filter dust immediately before the sucked air is discharged out of the robot cleaner 1. To prevent fine dust particles contained in the external air sucked in by the robot cleaner from being externally re-discharged, the third filter 330 may be a high efficiency particulate air (HEPA) filter in a structure like a folding screen, which appears to be wrinkled, and may, be a multi-HEPA filter.

The filter assembly 300 according to embodiments disclosed herein, as illustrated in FIG. 7, may be configured by employing at least one of the first filter 310, the second filter 320, or the third filter 330, or a combination thereof.

The filter assembly 300 may be detachable from one side surface of the dust container 30 or a front surface of the suction motor 2 within the robot cleaner 1. When the filter assembly 300 is attached in the robot cleaner 1, the first filter 310 may be mounted toward the dust container 30, namely, close to the dust container 30, and the third filter 330 may be mounted toward the suction motor 2, namely, close to the suction motor 20.

The plurality of conductive plates 340 and/or the porous structure 350 included in the filter assembly 300 may be located between the first filter 310 and the second filter 320, or between the second filter 320 and the third filter 330. The first to third filters 310 to 330, the plurality of conductive plates 340, and the porous structure 350, which may all be included in the filter assembly 300, may be arranged spaced by predetermined intervals, respectively.

Accordingly, an amount of dust piled on components (for example, the conductive plates 340, the porous structure 350, and the first to third filters 310 to 330) included in the filter assembly 300 or an amount of dust collected in the dust container 30 may be estimated based on the capacitance value between the conductive plates 340 measured by the calculator 120. Also, dust piled on the components included in the filter assembly 300 may be separated by an electric force, which may be generated by applying the AC current from the power supply 220 to at least a portion of a surface of the porous structure 350, thereby being collected in the dust container 30 or into a predetermined space within a robot cleaner, to or on which the dust container 30 may be mounted.

In such a manner, when the capacitance value measured with respect to the plurality of conductive plates 340 exceeds a predetermined value, the power supply 220 may apply power to the porous structure 350 in a periodic manner based on a predetermined time interval, or in response to an external input, thereby removing the dust piled on the conductive plates 340, the porous structure 350, or the first to third filters 310 to 330. This may result in overcoming a problem of lowering a suction force of the suction motor 2, which may be caused due to dust sucked in by the robot cleaner 1 through repetitive cleaning in a cleaning area.

Figure 8:
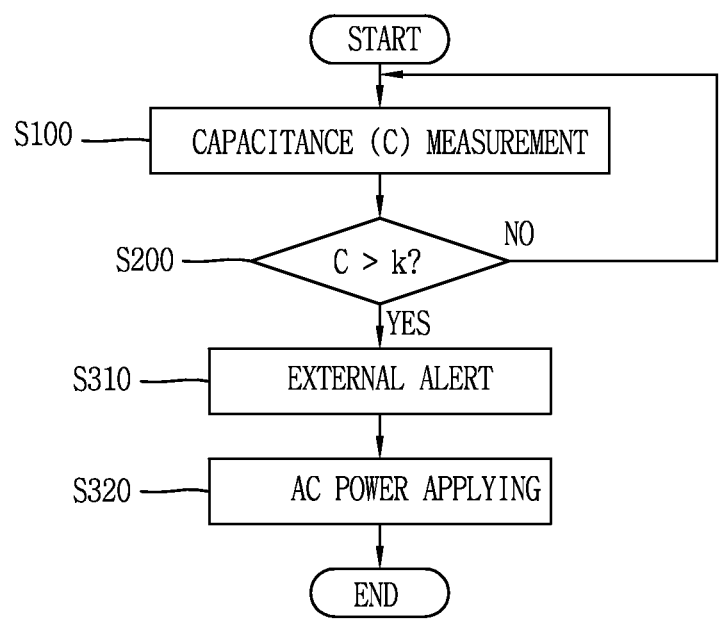
FIG. 8 is a flow chart of a method for sensing and/or removing dust in a robot cleaner in accordance with an embodiment.

FIG. 8 is a flow chart a method for sensing and/or removing dust in a robot cleaner in accordance with an embodiment. Hereinafter, the method will be described in detail with reference to FIGS. 1 to 7; however, repetitive description with respect the previous description has been omitted.

A method of sensing dust in a robot cleaner according to embodiments disclosed herein may include measuring a capacitance value between at least two conductive plates, such as conductive plates 340 of FIGS. 1 to 7, which may be spaced apart from each other so as to form a flow path of external air sucked in by the robot cleaner, in step S100. The capacitance value may change according to an amount of dust collected between the at least two conductive plates. A calculator, such as calculator 120 of FIGS. 1 to 7, may measure the capacitance value between the at least two conductive plates, thereby calculating an amount of dust piled on the at least two conductive plates and also an amount of dust piled on at least one filter located adjacent to the at least two conductive plates or collected in a dust container, such as dust container 30 of FIGS. 1-7.

The calculator may determine whether or not the capacitance value exceeds a predetermined value k, in step S200. When the capacitance value exceeds the predetermined value k, AC power may be applied to at least a portion of a surface of a porous structure, such as porous structure 210 of FIGS. 1-7, in step S320, to separate dust piled on the porous structure and/or at least one of a plurality of filters, such as first to third filters 310 to 330 of FIGS. 1-7, from them.

When the calculator carries out the determination as to whether or not the capacitance value exceeds the predetermined value k, it may repeat the calculation (measurement) of the capacitance value a plurality of times with a predetermined time interval therebetween. Accordingly, the calculator may determine whether the number of calculation reaches a predetermined number of times, for example, three times, so as to decide supply or non-supply of power to the porous structure using a power supply, such as power supply 220 of FIGS. 1-7. This may result in a more accurate determination as to whether dust collected between the at least two plates has exceeded a predetermined amount, thereby preventing an erroneous determination.

Whenever the calculator determines that the capacitance value has exceeded the predetermined value k, a number of times of the determination may be notified to the exterior by use of an indicator lamp, for example, or sound output through a speaker, for example. When the calculator determines that the capacitance value has exceeded the predetermined value k, the power supply may apply AC power to at least a portion of a surface of the porous structure (including at least a portion of an inner circumferential surface and/or an outer circumferential surface of a through hole), thereby separating the dust piled on the at least two conductive plates and/or the adjacent at least one filter.

When the power supply supplies n-phase AC power, such AC power may be applied to n-numbered conducting portions for each phase. Power with a phase difference by a predetermined phase angle may be supplied to each of conducting portions sequentially from one side of the porous structure, such that the dust may be smoothly separated from a laid portion (see FIG. 5).

Therefore, according to the method of sensing and/or removing dust of the robot cleaner according to embodiments disclosed herein, dust stuck on a filter may be removed or separated, thereby preventing a degradation of a suction performance of the suction motor, which may be caused due to dust piled on the filter.

Meanwhile, the calculator may measure the capacitance value so as to estimate an amount of dust collected in the dust container. Therefore, the method may further include notifying a user of a full collection of dust in the dust container in an audible or visible manner by making a notification member generate sound or light to the outside, when the capacitance value exceeds a predetermined value, in step S310. Consequently, the user may be guided to clean the conductive plates, the porous structure, and/or the at least one filter.

The method of sensing and/or removing dust of the robot cleaner according to embodiments disclosed herein may be implemented as computer-readable codes and recordable in a program-recorded medium. The computer-readable media may include programming command words, data files, and data structures, for example, in an individual or combination form. The programming command words recorded in the computer-readable media may be those specifically designed for embodiments disclosed herein or those already known by a skilled person in a computer software field. Examples of such computer-readable media may include hard disk, floppy disk, magnetic media such as magnetic tape, CD-ROM, optical data storage element, such as a DVD, magneto-optical media, such as a floptical disk, and hardware devices, such as a ROM, RAM, or flash memory, for example, which are specifically constructed to store and execute programming command words. Examples of the programming command words may include high-level language codes executable by computers using interpreter, for example as well as machine language made by compiler, for example. The hardware device may be configured to operate as at least one software module for executing processing according to embodiments, or a reverse case may also be similar.

Embodiments disclosed herein provide a robot cleaner, which is capable of sensing or removing dust on a filter, and a sensing method.

Embodiments disclosed herein further provide a robot cleaner that may include a suction motor installed within a main body and configured to generate a suction force, at least two conductive plates spaced apart from each other to form a flow path for external air introduced by the suction force, and a calculator configured to measure a capacitance value between the at least two conductive plates. The at least two conductive plates may be substantially parallel to each other. The at least two conductive plates may be arranged to be alongside of a flow direction of the air introduced from one side thereof.

The calculator may sense an amount of dust within a dust container of the robot cleaner based on the capacitance value. The robot cleaner may further include a notification member configured to generate sound or light to the exterior when the capacitance value exceeds a predetermined value.

Embodiments disclosed herein further provide a robot cleaner that may include a suction motor installed within a main body to generate a suction force, a porous structure provided with at least one through hole through which external air introduced by the suction force may flow, a filter disposed on a flow path of the air and configured to filter dust contained in the air, and a power supply unit or power supply configured to apply alternating current (AC) power to at least a partial surface of the porous structure. The filter may be disposed on one surface of the porous structure. The filter may be disposed to be spaced apart from the porous structure.

Further, the porous structure may be formed in a mesh shape. Also, the porous structure may have a honeycomb structure.

The porous structure may include at least one conducting portion formed along an inner circumferential surface and/or an outer circumferential surface of the at least one through hole. The power supply unit may apply n-phase AC power to the porous structure in a manner of applying power to each of n-numbered conducting portions for each phase. The power supply unit may apply power having a predetermined phase difference to the conducting portions based on predetermined single-phase power, sequentially in the order of positions of the conducting portions.

Embodiments disclosed herein also provide a filter assembly for a robot cleaner that may include at least two conductive plates that are disposed by being spaced apart from each other so as to form a flow path of external air introduced by the robot cleaner. A capacitance measured between the at least two conductive plates may vary due to dust collected between the at least two conductive plates. The filter assembly may further include a porous structure provided with at least one through hole through which the air may flow. The porous structure may receive alternating current (AC) power applied from the exterior to at least a partial surface thereof.

Embodiments disclosed herein also provide a filter assembly for a robot cleaner that may include a porous structure provided with at least one conductive through hole through which external air sucked by the robot cleaner may flow. At least a partial surface of the through hole may receive alternating current (AC) power applied from the exterior.

The filter assembly may further include a plurality of filters configured to filter dust particles in different sizes, contained in the air. One of the plurality of filters may be formed of cotton or a sponge in a pad shape. Also, one of the plurality of filters may be formed in a mesh shape. The plurality of filters may include a filter in a shape of a folding screen to filter off dust particles contained in the air.

Embodiments disclosed herein further provide a dust container configured to collect therein dust sucked in by a robot cleaner while the robot cleaner travels a cleaning area. A filter assembly for the robot cleaner may be installed at one side surface of the dust container.

Embodiments disclosed herein further provide a robot cleaner having a suction motor installed in a main body thereof to generate suction force. A filter assembly may be provided at an end of the suction motor.

Embodiments disclosed herein further provide a dust sensing method for a robot cleaner. The method may include measuring a capacitance between at least two conductive plates, which may be spaced apart from each other to form a flow path of external air introduced by the robot cleaner. The method may further include determining whether or not the capacitance exceeds a predetermined value.

The method may also include applying alternating current (AC) power to at least a partial surface of a porous structure through which the air may flow, when the capacitance exceeds the predetermined value. The method may further include generating sound or light when the capacitance exceeds the predetermined value.

Embodiments disclosed herein further provide a computer-readable medium in which a computer program for executing the dust sensing method for the robot cleaner may be recorded.

In a dust sensing and removing apparatus and method for a robot cleaner according to embodiments, dust collected on a filter may be separated, so as to prevent a suction performance of a suction motor from being lowered due to the dust collected on the filter.

As the present features may be embodied in several forms without departing from the characteristics thereof, it should also be understood that the above-described embodiments are not limited by any of the details of the foregoing description, unless otherwise specified, but rather should be construed broadly within its scope as defined in the appended claims, and therefore all changes and modifications that fall within the metes and bounds of the claims, or equivalents of such metes and bounds are therefore intended to be embraced by the appended claims.

Any reference in this specification to "one embodiment," "an embodiment," "example embodiment," etc., means that a particular feature, structure, or characteristic described in connection with the embodiment is included in at least one embodiment of the invention. The appearances of such phrases in various places in the specification are not necessarily all referring to the same embodiment. Further, when a particular feature, structure, or characteristic is described in connection with any embodiment, it is submitted that it is within the purview of one skilled in the art to effect such feature, structure, or characteristic in connection with other ones of the embodiments.

Although embodiments have been described with reference to a number of illustrative embodiments thereof, it should be understood that numerous other modifications and embodiments can be devised by those skilled in the art that will fall within the spirit and scope of the principles of this disclosure. More particularly, various variations and modifications are possible in the component parts and/or arrangements of the subject combination arrangement within the scope of the disclosure, the drawings and the appended claims. In addition to variations and modifications in the component parts and/or arrangements, alternative uses will also be apparent to those skilled in the art.

What is claimed is:

1. A robot cleaner, comprising:
   a suction motor installed within a main body and configured to generate a suction force;
   a dust sensing apparatus comprised of at least two conductive plates spaced apart from each other to form a flow path for external air introduced by the suction force; and
   a calculator that measures a capacitance value between the at least two conductive plates;
   wherein the at least two conductive plates are disposed substantially parallel to each other, and
   wherein a space, which is formed as the at least two conductive plates are spaced apart from each other, forms a flow path for air sucked in by the robot cleaner.

2. The robot cleaner of claim 1, wherein the at least two conductive plates are arranged to extend along of a flow direction of the air introduced from one side thereof.

3. The robot cleaner of claim 1, wherein the calculator senses an amount of dust within a dust container of the robot cleaner based on the capacitance value.

4. The robot cleaner of claim 1, further comprising:
   a notification member to generate sound or light to an exterior of the robot cleaner when the capacitance value exceeds a predetermined value.

5. The robot cleaner of claim 1, further comprising
   a porous structure provided with at least one through hole through which external air introduced by the suction force flows;
   at least one filter disposed in the flow path of the air, to filter dust contained in the air; and
   a power supply configured to apply alternating current (AC) power to at least a portion of a surface of the porous structure.

6. The robot cleaner of claim 1, wherein the at least two conductive plates comprise a plurality of first conductive plates and a plurality of second conductive plates, the plurality of the first and second conductive plates being alternately provided and disposed in parallel.

7. The robot cleaner of claim 6, wherein the plurality of first conductive plates is connected by a first connector and the plurality of second conductive plates is connected by a second connector.

* * * * *